US009688589B2

(12) United States Patent
Barve et al.

(10) Patent No.: US 9,688,589 B2
(45) Date of Patent: Jun. 27, 2017

(54) PROCESS FOR PREPARATION OF N-PROPYL BENZENE

(71) Applicant: VINATI ORGANICS LIMITED, Mumbai (IN)

(72) Inventors: Prashant Purushottam Barve, Pune (IN); Jayesh Ajitkumar Ashar, Mumbai (IN)

(73) Assignee: VINATI ORGANICS LIMITED, Mumbai (IN)

(*) Notice: Subject to any disclaimer, the term of this patent is extended or adjusted under 35 U.S.C. 154(b) by 71 days.

(21) Appl. No.: 14/563,701

(22) Filed: Dec. 8, 2014

(65) Prior Publication Data

US 2016/0046543 A1 Feb. 18, 2016

(30) Foreign Application Priority Data

Aug. 13, 2014 (IN) .......................... 2609/MUM/2014

(51) Int. Cl.
*C07C 2/72* (2006.01)
*C07C 2/54* (2006.01)

(52) U.S. Cl.
CPC ............ *C07C 2/72* (2013.01); *C07C 2523/04* (2013.01); *C07C 2527/232* (2013.01); *Y02P 20/52* (2015.11)

(58) Field of Classification Search
None
See application file for complete search history.

(56) References Cited

U.S. PATENT DOCUMENTS 2,748,178 A * 5/1956 Pines ...................... C07C 2/72
546/181
3,006,976 A * 10/1961 Shaw ...................... C07C 2/24
159/DIG. 10
4,179,471 A * 12/1979 Cobb ...................... C07C 2/72
585/411

(Continued)

OTHER PUBLICATIONS

Pines et al., Sodium Catalyzed Reactions. II. Side-chain Ethylation of Alkyl Aromatic Hydrocarbons Catalyzed by Sodium, J. Am. Chem. Soc., 77, 1955, pp. 554-559.*

(Continued)

*Primary Examiner* — In Suk Bullock
*Assistant Examiner* — Philip Louie
(74) *Attorney, Agent, or Firm* — Wiley Rein LLP

(57) ABSTRACT

Disclosed is a process for preparation of n-propyl benzene. The process gives high selectivity and yield of n-propyl benzene by single step catalytic alkylation that involves contacting a mixture of aromatic hydrocarbon having an active hydrogen on a saturated α-carbon, such as toluene, and an alkene, such as ethylene, in presence of a metal catalyst, a solid support, and an initiator. Following the alkylation, aqueous and organic phases are separated from a reaction mixture. The aqueous phase is separated for recovery of the catalyst, the solid support, and un-reacted aromatic hydrocarbon (e.g., toluene); and the organic phase is separated for obtaining n-propyl benzene and byproduct. Thus, the catalyst phase can be recovered and recycled in the next alkylation reaction. Also, the process facilitates recovery and recycling of the byproduct for the better selectivity.

7 Claims, 1 Drawing Sheet

(56) References Cited

U.S. PATENT DOCUMENTS 5,157,186 A * 10/1992 Staton .................. B01J 27/232
                                                                585/453
2010/0145121 A1* 6/2010 Belmont ................. C07C 2/72
                                                                585/453

OTHER PUBLICATIONS

Claff, C. E et al., "The Metalation of Toluene by Potassium and Sodium," J. Org. Chem 1955, 20(4):440-442.
Pines, H. et al., "Sodium- and Potassium-Catalyzed Reactions of Toluene, Ethylbenzene, and Isopropylbenzene with Isoprene," J. Org. Chem., 1965, 30(1)280-284.
Schramm, R. M. et al, "The Alkali Metal Catalyzed Alkylation of Toluene with Propylene," J. Am. Chem. Soc. 1960, 82(18):4912-4918.

\* cited by examiner

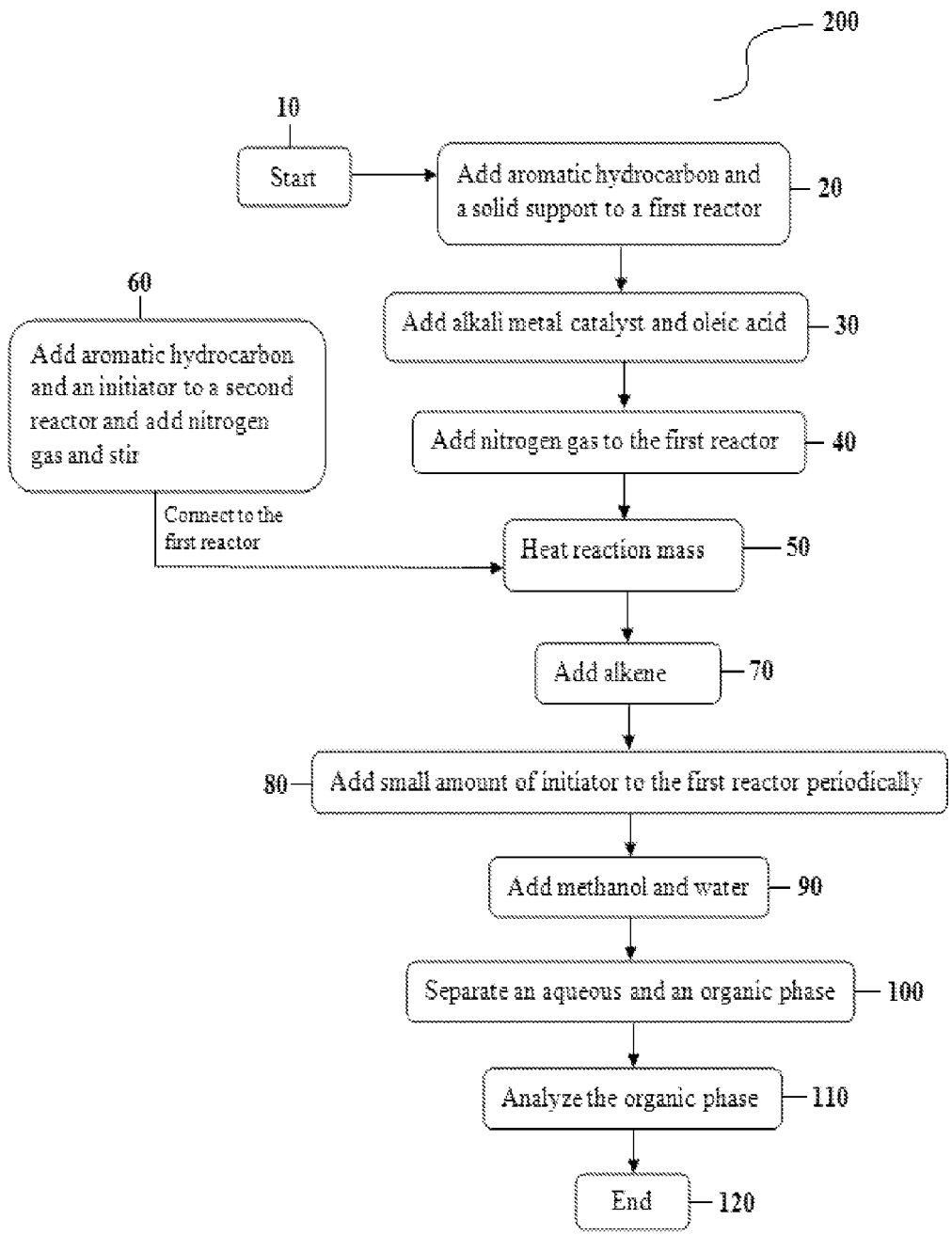

PROCESS FOR PREPARATION OF N-PROPYL BENZENE

RELATED APPLICATIONS

This application claims priority benefit of Indian Patent Application No. 2609/MUM/2014, filed 13 Aug. 2014 and incorporated fully herein for all purposes.

FIELD OF THE INVENTION

The present invention relates to an alkylation and more particularly, to a process for preparation of n-propyl benzene.

BACKGROUND

Alkyl benzenes are useful, for example as intermediates in the production of various end products. It has been known for decades that alkali metals, when reacted with alkyl benzenes, displace benzylic hydrogens. Chester E. Claff & Avery A. Morto, 20 J. Org. Chem. 440 (1955); Herman Pines & Norman C. Sih, 30 J. Org. Chem. 280 (1965); Schramm & Langlois, 82 J. Am. Chem. Soc'y 4912 (1960). The resulting alkyl benzene anion and alkali metal cation pair undergoes a reaction with olefins at high temperature to give alkylation products in which single or all saturated benzylic carbon atoms are alkylated in such a way as to replace single or all of the benzylic hydrogen atoms on a carbon atom with one aliphatic chain per benzylic hydrogen atom. Such reactions yield a variety of products depending on the number of saturated benzylic carbon atoms and the number of hydrogen atoms on the given benzylic carbon atom. In the commercial production of alkyl benzenes, high purity product is generally desired and byproducts must be removed.

Several patents and publications address issues related to providing suitable methods for commercial production of alkyl benzenes for example, U.S. Pat. No. 8,277,652 B2, U.S. Pat. No. 6,100,437, and U.S. Pat. No. 4,950,831.

The examples cited in U.S. Pat. No. 8,277,652 B2 and U.S. Pat. No. 6,100,437 employ sodium-potassium alloy as the catalyst. The catalyst, during activation step, gets melted but remains as a different phase than the alkyl benzene. This helps metalation of alkyl benzene. Also, the use of a small amount of water in the reaction is mentioned in this process. This operation poses difficulties as follows:

The small amount of catalyst causes inefficient distribution of the catalyst in the alkane phase.
High temperature promotes the tarry byproducts which cover the catalyst surface and the reaction is lowered.
Also, the use of sodium-potassium alloy in presence of water is hazardous and affects the process economics.

A serious problem with the present alkali metal especially sodium-potassium alloy catalyzed alkylation reaction is the fact that an alpha carbon of the alkyl benzene anion can add to either carbon atom comprising the olefinic double bond thereby giving two alkylation products. Moderation of reaction conditions has proven to be effective in eliminating multiple alkylations.

Inability to conveniently improve upon addition selectivity, however, is a problem. In addition to multiple alkylation of the alkyl benzene, the alkali metal catalyst utilized in the alkylation reaction seems to promote insoluble tarry byproducts formation due to poly condensation or the alkali metal catalyzed polymerization reaction. Other byproducts are also formed in the alkali metal catalyzed reactions which are soluble in reaction medium offering darkened color to the reaction medium.

Yet another problem in the present alkali metal catalyzed reaction is the proper distribution of the alkali metal alloy in the reaction system. Reference may be made to U.S. Pat. No. 8,277,652 B2, wherein 0.5 wt % of the sodium-potassium alloy is used as the catalyst. The alloy is used in the neat form and it is highly difficult to disperse the small quantity of the catalyst uniformly throughout the reaction medium which is destroyed at the end of the reaction. In order for reaction efficiency, the alkyl benzene-potassium ion pair, formed in the reaction between the alkyl benzene and potassium, should be dispersed effectively in the reaction mixture to get good selectivity for mono-alkylation.

The alkyl benzene-potassium ion pair and the alkyl benzenes form immiscible phases and the malfunctioning of the catalyst distribution in the reaction media leads to the side product formation. Generally, the present system being practiced commercially uses small amount of tall oil and water to help the catalyst and associated catalytic species in emulsified phase in the reaction medium. The small amount of water used in the present commercial practice to emulsify the reaction medium poses a serious safety concern.

It is generally believed that the alkyl benzene-potassium ion pair that is a catalyst complex gets dispersed at the emulsified phase which also coats the alkali metal alloy, thus higher surface area is available for the reaction with an alkene. The formation of tars and other byproducts reduces reactant utilization significantly. The formation of tars and other byproducts has further commercial impact in that the alkyl benzene-potassium ion pair gets covered by the tarry product, which reduces the rate of formation of alkyl benzene though the catalyst is active. Additionally, the active catalyst covered by the tarry product gets destroyed at the end of production cycle by water. This puts severe pressure on ecology and the process economics.

Similarly, with the current alkali metal alloy system, in which the alkyl benzenes are isolated after aqueous work-up that takes place towards end of the reaction, water is charged followed by layer separation. This causes troublesome emulsion formation due to high alkalinity of reaction medium, and causes loss of costly alkali metal alloy: the heavy emulsion tends to lose the organic phase. This puts severe pressure on ecology and the process economics.

Schramm and Langlois (1960) presented a detailed study of the alkylation of toluene using propylene as the form of alkene in the presence of highly dispersed sodium or potassium or lithium metal and various activators, such as anthracene, fluorene, indene, cyclopentadiene, α-methyl pyridine, and the like, as the chain initiator and shown that the alkylation of alpha carbon atom takes place at 149° C. to 307° C.

Schramm and Langlois also presented a detailed study of the effects of alkali metals on the yield of byproducts, particularly isomers due to non-selective addition at the double bond at a wide range of temperatures. They observed a lower product-to-isomer ratio over a temperature range of 107° C. to 204° C. in the presence of potassium as the catalyst. Alternatively, when sodium was used instead of potassium, the product-to-isomer ratio was large. Also, their data showed that in the presence of potassium as the catalyst, the rate of product formation was higher than in presence of sodium as the catalyst.

Herman Pines and Norman C. Sih (1965) presented a detailed study of alkylation of toluene, ethyl benzene and isopropyl benzene, using isoprene as the form of alkene in presence of highly dispersed sodium or potassium metal and o-chlorotoluene as a chain initiator; and showed that the alkylation of alpha carbon atom takes place at 125° C. to 133° C. in the presence of an initiator such as o-chlorotoluene.

Also, in a current industrial practice, higher amounts of catalysts, such as potassium metal and sodium metal alloy, are used in the pre-alkylation stage that gets destroyed by putting water or alcohol at the end of the cycle.

Accordingly, there is a need to provide a process for preparation of n-propyl benzene that overcomes the drawbacks of the prior art.

SUMMARY

An aspect of the present embodiments provides for use of initiators that improve selectivity of starting aromatic hydrocarbons towards a desired product.

Another aspect of the present embodiments facilitates reuse of a metal catalyst and higher alkylated products.

Another aspect of the present embodiments provides for recycling of a byproduct, thereby increasing selectivity towards the desired product.

Accordingly, the present embodiments provide a process for preparation of n-propyl benzene. The process may involve adding an aromatic hydrocarbon having an active hydrogen on a saturated α-carbon and a solid support to a first reactor to form a mixture. Further, the process may involve adding an alkali metal catalyst and oleic acid to the mixture to form a reaction mass, and closing and agitating the first reactor for a predefined period of time. The alkali metal catalyst can be selected from sodium, lithium, or a combination thereof. Furthermore, the process may involve flushing nitrogen gas into the first reactor, and heating the reaction mass at a temperature in a range of about 185° C. to about 190° C. for about 15 minutes. Moreover, the process may involve adding an aromatic hydrocarbon and an initiator to a second reactor. The initiator can be any one of di-ter-butyl peroxide, azo-iso-bis butyronitrile, or iso-amyl nitrite. The initiator can be used in a range of 50 ppm to 100 ppm, in single stage or in multiple stages. The second reactor may then be flushed with nitrogen gas, and contents of the second reactor maintained under stirring for a predefined period of time. Then, the second reactor, via a bottom liquid discharge valve, may be connected to the first reactor.

Further, the process may involve adding an alkene, for example ethylene, to the first reactor to form a reaction mixture. Furthermore, the process may involve periodically adding a small amount of initiator to the first reactor, and maintaining the reaction mixture at a temperature in a range of about 180° C. to 220° C. for longer than 1 hour to 5 hours, while agitating the reaction mixture at about 35 kg/cm² to about 40 kg/cm². Moreover, the process may involve adding a desired amount of methanol and water to the reaction mixture. Further, the process may involve separating an aqueous phase for recovery of the catalyst, catalyst support and un-reacted toluene; and separating an organic phase for obtaining n-propyl benzene and byproduct. Furthermore, the process may involve analyzing and purifying the organic phase to obtain n-propyl benzene.

Moreover, the process may involve recovering from the reaction mixture un-reacted aromatic hydrocarbon having the active hydrogen on the saturated α-carbon, and using at least a portion of the recovered un-reacted hydrocarbon in the preparation of n-propyl benzene.

BRIEF DESCRIPTION OF THE DRAWING

FIG. 1 shows a flowchart illustrating a process for preparation of n-propyl benzene, in accordance with the present invention.

DETAILED DESCRIPTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The various aspects of the invention are accomplished, and the problems and shortcomings associated with the prior art techniques and approaches thereof are overcome, by the embodiments as described below.

The present embodiments provide a process for preparation of n-propyl benzene. In one embodiment, the process gives high selectivity and yield of n-propyl benzene by single-step catalytic alkylation that involves contacting a mixture of toluene and ethylene, over an alkali metal such as lithium or sodium and alkali metal carboxylate like potassium carbonate, in presence of initiators/promoters such as di-ter-butyl peroxide (DTBP), azo-iso-bis butyronitrile (AIBN), and iso-amyl nitrite.

Referring to FIG. 1, an embodiment of the invention provides a process (200) for preparation of n-propyl benzene. The process (200) starts at step (10). At step (20), the process (200) involves adding aromatic hydrocarbon and a solid support to a first reactor to form a mixture. In one embodiment, the aromatic hydrocarbon includes an active hydrogen on a saturated α-carbon, for example toluene. The solid support can be an alkali metal carboxylate, for example potassium carbonate powder, that acts as a medium for spreading an alkali metal catalyst thereon.

At step (30) of an embodiment, the process (200) involves adding alkali metal catalyst and oleic acid as a dispersing agent to the mixture to form a reaction mass. The alkali metal catalyst can be selected from sodium, lithium, or a combination thereof. In an embodiment, molten sodium metal or lithium metal can be used and coated on the solid support. After addition of the alkali metal catalyst and oleic acid, the first reactor can be closed and agitated for a time period of about 30 minutes to about 1 hour.

At step (40), the process (200) of an embodiment may involve flushing nitrogen gas to the first reactor, which creates inertness therein. At step (50), the process (200) may involve heating the reaction mass at a temperature in a range of about 185° C. to about 190° C. for about 15 minutes.

At step (60), the process (200) may involve adding an aromatic hydrocarbon and an initiator to a second reactor. In a particular embodiment, the aromatic hydrocarbon is toluene. The initiator may be selected from di-ter-butyl peroxide, azo-iso-bis butyronitrile, iso-amyl nitrite, or a combination thereof. The nitrogen gas can then be flushed inside the second reactor, and the contents of the second reactor kept under stirring for a time period of about 15 minutes to about 30 minutes. Then, a bottom liquid discharge valve of the second reactor can be connected to the first reactor.

At step (70) shown in FIG. 1, the process (200) may involve adding an alkene to the first reactor to form a reaction mixture. In a particular embodiment, the alkene is ethylene.

At step (80), the process (200) may involve periodically adding a small amount of the initiator to the first reactor. The reaction may be continued until a desired consumption of ethylene is observed. The reaction mixture can be maintained at a temperature in a range of about 180° C. to about 220° C. for longer than 1 hour to 5 hours while agitating the reaction mixture at about 35 kg/cm2 to about 40 kg/cm2. Once the desired consumption of ethylene is observed, the reaction mixture may be cooled to room temperature.

At step (90), the process (200) may involve adding desired amount of methanol and water to the reaction mixture. The reaction mixture may then be taken out of the first reactor.

At step (100), the process (200) may involve separating an aqueous phase and an organic phase from the reaction mixture. The aqueous phase can be separated for recovery of the catalyst, catalyst support, and un-reacted toluene; and the organic phase can be separated for obtaining n-propyl benzene and byproduct. At step (110), the process (200) may involve analyzing the organic phase. In a particular embodiment, the organic phase is analyzed by gas chromatography (hereinafter "the GC"). The purity of n-propyl benzene has been found to be 99.82% by the GC analysis. The process (200) ends at step (120).

The process embodied in FIG. 1 (200) facilitates recovery of aromatic hydrocarbon, alkali metal catalyst, and byproduct. The process (200) utilizes different kinds of initiators, such as di-tert-butyl peroxide (DTBP), azo-iso-bis-butyronitrile (AIBN), and iso-amyl-nitrite. The initiators can be used as intermittent charging into the reaction mass. In accordance with the present embodiments, in the process (200) for preparation of n-propyl benzene, 3-pentyl benzene is formed as the byproduct. Most of the chemical reactions are equilibrium-controlled, and the formation of the byproduct also is equilibrium-controlled. In addition, in the process (200), few experiments are carried out; wherein 3-pentyl benzene along with toluene was charged deliberately in the reaction system that resulted in increase in selectivity of the process (200) towards n-propyl benzene.

In an embodiment of the process (200), among the products that can be synthesized more efficiently using alkyl benzenes, such as iso-butyl benzene, prepared in accordance with this embodiment, include members of the family of compounds that comprise the 2-aryl propionic acid derivatives. Specially, ibuprofen, a commercially successful, over-the-counter analgesic, can be synthesized using isobutyl benzene prepared as a raw material. Similarly, in another embodiment, among the products that can be synthesized more efficiently using alkyl benzenes, include 3-isobutyl-toluene and sec-butyl benzene, starting from m-xylene-propylene and ethylbenzene-ethylene, respectively.

The embodiments are further illustrated hereinafter by means of examples.

EXAMPLES

Example 1

Preparation of n-Propyl Benzene Using Potassium Carbonate as the Solid Support for Sodium Catalyst without Initiator (Control Experiment)

The first reactor is a 2 liter capacity high-pressure stirred reactor. To the first reactor, dry toluene, dry potassium carbonate, sodium metal catalyst and oleic acid as the dispersing agent were added. The first reactor was then closed, and the agitation of the first reactor was started. The first reactor was flushed with nitrogen gas. Then the reaction mass was heated for 15 minutes at a temperature in a range of about 185° C. to about 190° C. to activate the catalyst.

Meanwhile, a small amount of dry toluene was taken in the second reactor. The second reactor is a 500-ml capacity stirred high pressure reactor. Nitrogen was flushed to the contents of the second reactor and kept under stirring. The bottom liquid discharge valve of the second reactor was connected to the first reactor and the vents of both of the reactors were connected.

Once the desired reaction temperature of the first reactor was attained, a desired amount of ethylene was added to the first reactor with the help of ethylene cylinder. The addition of ethylene caused the pressure of the first reactor to rise initially and subside slowly as the ethylene consumption took place. The reaction was continued until desired consumption of ethylene was observed, and then the reaction mass was cooled to room temperature. To the reaction mass, a desired amount of methanol followed by water was added. The reaction mixture was taken out of the first reactor, and a lower aqueous phase and an upper organic phase were separated. The organic phase was analyzed using GC. The GC model used was Shimadzu-17 A, the Column used was DB Petro 100 m length (ID 0.25 mm, film thickness 0.5 micron), FID detector, Injector temperature 250° C., Detector temperature 260° C., Initial temperature 80° C., hold time 2 minutes, heating rate 4° C./min, final temperature 250° C. for 30 minutes, nitrogen flow rate 1.4 ml/min, split ratio 1:80. The results of the various examples are as shown in the following Table-1.

TABLE 1

Examples - 1.1 and 1.2 using potassium carbonate as catalyst support

| | Example Number | |
|---|---|---|
| | Example-1.1 | Example-1.2 |
| Charge to 2-L Reactor | | |
| Dry toluene, gm | 922 | 920 |
| Ethylene Gas | | |
| Lot-1, gm | 98 | 70 |
| Lot-2, gm | 43 | 70 |
| Potassium carbonate, gm | 78 | 78 |
| Sodium metal, gm | 9.2 | 9.2 |
| Oleic acid, gm | 2.5 | 2.5 |
| Methanol, gm | 32 | 32 |
| Water, gm | 600 | 600 |
| Charge to 500-ml Reactor | | |
| Dry toluene | 0 | 184 |
| Process conditions | | |
| Maximum reaction temp., °C | 180.9 | 210.1 |
| Maximum reaction press., kg/cm$^2$ | 30.7 | 44.8 |
| Final reaction press., kg/cm$^2$ | 7.6 | 9.5 |
| Reaction time in hr | 4.5 | 5 |
| Output of reaction mass | | |
| Wt. of organic layer, gm | 904 | 1181 |
| Wt of aqueous layer, gm | 698 | 694 |
| Analysis, wt % | | |
| Hexenes, wt % | 0.085 | 0 |
| Toluene, wt % | 80.889 | 61.453 |
| n-Propyl Benzene (NPB), wt % | 15.891 | 23.821 |
| 3-PP (**) and Heavies, wt % | 2.997 | 14.726 |
| Reaction performance | | |
| Toluene to Ethylene mol ratio | 1.99 | 2.40 |
| Quantity of NPB, gm | 143.65 | 281.33 |
| Selectivity based on toluene, % | 57.76 | 57.02 |
| Toluene per pass conversion, % | 20.68 | 34.26 |
| NPB to 3-PP & Heavies ratio | 5.3 | 1.62 |

Example 2

Preparation of n-Propyl Benzene Using Potassium Carbonate as the Solid Support for Sodium Catalyst and the Initiator The first reactor was a 2 liter capacity high pressure stirred reactor. To the first reactor, dry toluene, dry potassium carbonate, sodium metal catalyst, and oleic acid (as the dispersing agent), was added. The first reactor was then closed and the agitation of the first reactor was started. The first reactor was flushed with nitrogen gas. Then the reaction mass was heated for 15 minutes at temperature in a range of about 185° C. to about 190° C. to activate the catalyst.

Meanwhile, about 184 gm of dry toluene was taken in the second reactor and 50 ppm to 100 ppm of di-ter-butyl peroxide (DTBP) (as the initiator) was added thereto. The second reactor was a 500-ml capacity stirred high-pressure reactor. The nitrogen was flushed to the contents of the second reactor and kept under stirring. The bottom liquid discharge valve of the second reactor was connected to the first reactor, and the vents of both the reactors were connected.

Once the desired reaction temperature of the first reactor was attained, a desired amount of ethylene was added to the first reactor with the help of ethylene cylinder. The addition of ethylene caused the pressure of the first reactor to rise initially and subside slowly as the ethylene consumption took place. The reaction was continued until a desired consumption of ethylene was observed, and then the reaction mass was cooled to room temperature. To the reaction mass, a desired amount of methanol followed by water was added. The reaction mixture was taken out of the first reactor, and a lower aqueous phase and an upper organic phase were separated. The organic phase was analyzed using the GC as mentioned in Example 1. The details and the results of the examples 2.1 to 2.8 are shown in the following Table-2.

TABLE 2

Examples - 2.1 to 2.8: potassium carbonate as catalyst support with DTBP as initiator

| | Example Number: | | | |
|---|---|---|---|---|
| | Example-2.1 | Example-2.2 | Example-2.3 | Example-2.4 |
| Charge to 2-L Reactor | | | | |
| Dry toluene, gm | 922 | 922 | 922 | 922 |
| Ethylene Gas | | | | |
| Lot-1, gm | 70 | 140 | 140 | 90 |
| Lot-2, gm | 70 | | | 10 |
| Potassium carbonate, gm | 78 | 78 | 78 | 78 |
| Sodium metal, gm | 8.7 | 9.2 | 9.2 | 9.2 |
| Oleic acid, gm | 2.5 | 2.5 | 2.5 | 2.5 |
| Methanol, gm | 32 | 32 | 32 | 32 |
| Water, gm | 600 | 600 | 600 | 600 |
| Charge to 500-ml Reactor | | | | |
| Dry toluene | 184 | 184 | 184 | 184 |
| Initiator, DTBP(*), mg | 60 | 120 | 60 | 60 |
| Process conditions | | | | |
| Maximum reaction temp., °C | 182.2 | 185.5 | 190.8 | 190.6 |
| Maximum reaction press., kg/cm$^2$ | 36.6 | 32.2 | 37.8 | 33 |
| Final reaction press., kg/cm$^2$ | 11.3 | 7.6 | 9.3 | 12.1 |
| Reaction time in hr | 2.45 | 3 | 3 | 3.25 |

TABLE 2-continued

Examples - 2.1 to 2.8: potassium carbonate as catalyst support with DTBP as initiator

| Output of reaction mass | | | | |
|---|---|---|---|---|
| Wt. of organic layer, gm | 1106 | 1115 | 1149 | 1117 |
| Wt of aqueous layer, gm | 707 | 702 | 718 | 703 |
| Analysis, wt % | | | | |
| Hexenes, wt % | 0.12 | 0.077 | 0.025 | 0.1037 |
| Toluene, wt % | 73.86 | 78.346 | 55.97 | 72.6199 |
| n-Propyl Benzene (NPB), wt % | 21.2 | 17.327 | 32.91 | 20.6993 |
| 3-PP (**) and Heavies, wt % | 4.41 | 4.014 | 10.966 | 6.42 |
| Reaction performance | | | | |
| Toluene to Ethylene mol ratio | 2.40 | 2.40 | 2.40 | 3.36 |
| Quantity of NPB, gm | 234.47 | 193.20 | 378.14 | 231.21 |
| Selectivity based on toluene, % | 62.61 | 64.28 | 62.9 | 60.53 |
| Toluene per pass conversion, % | 26.01 | 20.87 | 41.75 | 26.52 |
| NPB to 3-PP & Heavies ratio | 4.81 | 4.32 | 3.01 | 3.22 |

| | Example Number: | | | |
|---|---|---|---|---|
| | Example-2.5 | Example-2.6 | Example-2.7 | Example-2.8 |
| Charge to 2-L Reactor | | | | |
| Dry toluene, gm | 920 | 920 | 920 | 920 |
| Ethylene Gas | | | | |
| Lot-1, gm | 45 | 140 | 50 | 45 |
| Lot-2, gm | 48 | | 75 | 48 |
| Potassium carbonate, gm | 78 | 78 | 78 | 78 |
| Sodium metal, gm | 8.7 | 9.2 | 9.2 | 9.2 |
| Oleic acid, gm | 2.5 | 2.5 | 2.5 | 2.5 |
| Methanol, gm | 32 | 32 | 32 | 32 |
| Water, gm | 600 | 600 | 600 | 600 |
| Charge to 500-ml Reactor | | | | |
| Dry toluene | 184 | 184 | 184 | 184 |
| Initiator, DTBP (*), mg | 120 | 65 | 62 | 60 |
| Process conditions | | | | |
| Maximum reaction temp., °C. | 190.1 | 195.34 | 195.4 | 192.4 |
| Maximum reaction press., kg/cm$^2$ | 18.6 | 31.8 | 34.2 | 38.7 |
| Final reaction press., kg/cm$^2$ | 8.7 | 9.2 | 11.8 | 10.3 |
| Reaction time in hr | 3 | 3.5 | 3.25 | 3.5 |
| Output of reaction mass | | | | |
| Wt. of organic layer, gm | 1109 | 1134 | 1143.2 | 1107 |
| Wt of aqueous layer, gm | 699 | 698 | 702 | 545 |
| Analysis, wt % | | | | |
| Hexenes | 0.086 | 0.076 | 0.0863 | 0.3792 |
| Toluene | 80.7862 | 63.93 | 62.5214 | 62.975 |
| n-Propyl Benzene (NPB) | 15.5083 | 24.6894 | 25.364 | 24.87 |
| 3-PP (**) and Heavies | 3.4307 | 11.1819 | 11.898 | 11.62 |
| Reaction performance | | | | |
| Toluene to Ethylene mol ratio | 3.61 | 2.40 | 2.69 | 3.61 |
| Quantity of NPB, gm | 171.99 | 279.98 | 289.96 | 275.31 |
| Selectivity based on toluene | 63.37 | 56.63 | 57.11 | 51.88 |
| Toluene per pass conversion | 18.85 | 34.33 | 35.26 | 36.85 |
| NPB to 3-PP & Heavies ratio | 4.52 | 2.21 | 2.13 | 2.14 |

(*) DTBP-Di-tert-butyl peroxide;

(**) 3-Phenyl pentane.

Example 3

Preparation of n-Propyl Benzene Using Potassium Carbonate as the Solid Support for Sodium Catalyst with the Initiator In this example, preparation of n-propyl benzene was carried out using potassium carbonate as the solid support, sodium as the metal catalyst and azo-iso-bis butyronitrile (AIBN) as the initiator. The steps of the process (200) are similar as mentioned in example 2 and the same are not again described herein for the sake of the brevity of the invention. The details and the results of the examples 3.1-3.3 are shown in the following Table-3.

TABLE 3

Examples 3.1 to 3.3: potassium carbonate as catalyst support, AIBN as initiator

| | Example Number | | |
|---|---|---|---|
| | Example-3.1 | Example-3.2 | Example-3.3 |
| Charge to 2-L Reactor | | | |
| Dry toluene, gm | 920 | 920 | 920 |
| Ethylene Gas | | | |
| Lot-1, gm | 135 | 120 | 165 |
| Lot-2, gm | | | |
| Potassium carbonate, gm | 78 | 78 | 78 |
| Sodium metal, gm | 9.2 | 9.2 | 9.2 |
| Oleic acid, gm | 2.7 | 2.7 | 2.7 |
| Methanol, gm | 32 | 30 | 30 |
| Water, gm | 604 | 600 | 600 |
| Charge to 500-ml Reactor | | | |
| Dry toluene | 184 | 184 | 184 |
| Initiator, AIBN (*), mg | 64 | 60 | 60 |
| Process conditions | | | |
| Maximum reaction temp., ° C. | 221.8 | 190.8 | 195.2 |
| Maximum reaction press., kg/cm$^2$ | 53.4 | 37.4 | 46.3 |
| Final reaction press., kg/cm$^2$ | 16.4 | 19.9 | 13.2 |
| Reaction time in hr | 3.5 | 4.25 | 4.25 |
| Output of reaction mass | | | |
| Wt. of organic layer, gm | 1198 | 1118 | 1190 |
| Wt of aqueous layer, gm | 707 | 698 | 701 |
| Analysis, wt % | | | |
| Hexenes, wt % | 0.1849 | 0.2191 | 0.0808 |
| Toluene, wt % | 54.5393 | 69.9528 | 55.2322 |
| n-Propyl Benzene (NPB), wt % | 27.9853 | 21.6334 | 28.274 |
| 3-PP (**) and Heavies, wt % | 16.981 | 8.0656 | 16.2886 |
| Reaction performance | | | |
| Toluene to Ethylene mol ratio | 2.49 | 2.80 | 2.04 |
| Quantity of NPB, gm | 335.26 | 241.86 | 336.46 |
| Selectivity based on toluene, % | 57.04 | 57.60 | 57.74 |
| Toluene per pass conversion, % | 40.82 | 29.16 | 40.47 |
| NPB to 3-PP & Heavies ratio | 1.65 | 2.68 | 1.74 |

(*) AIBN-Azo-Iso-bis Butyro Nitrile;
(**) 3-Phenyl pentane.

Example 4

Preparation of n-Propyl Benzene Using Potassium Carbonate as the Solid Support for Sodium Catalyst with the Initiator In this example, preparation of n-propyl benzene was carried out using potassium carbonate as the solid support, sodium as the metal catalyst, and iso-amyl nitrite as the initiator. The steps of the process (200) are similar as mentioned in Example 2, and the same are not again described herein for the sake of the brevity. The details and the results of the examples 4.1-4.3 are shown in the following Table-4.

TABLE 4

Examples-4.1 to 4.3: potassium carbonate as catalyst support, iso-amyl nitrite as initiator

| | Example Number | | |
|---|---|---|---|
| | Example-4.1 | Example-4.2 | Example-4.3 |
| Charge to 2-L Reactor | | | |
| Dry toluene, gm | 920 | 920 | 920 |
| Ethylene Gas | | | |
| Lot-1, gm | 95 | 127 | 127 |
| Lot-2, gm | | | |
| Potassium carbonate, gm | 78 | 78 | 78 |
| Sodium metal, gm | 9.3 | 9.18 | 9.18 |
| Oleic acid, gm | 2.5 | 2.5 | 2.5 |
| Methanol, gm | 32 | 32 | 32 |
| Water, gm | 604 | 600 | 600 |
| Charge to 500-ml Reactor | | | |
| Dry toluene | 184 | 184 | 184 |
| Initiator, iso-Amyl Nitrite, mg | 120 | 64 | 64 |
| Process conditions | | | |
| Maximum reaction temp., ° C. | 195.5 | 195.1 | 195.1 |
| Maximum reaction press. kg/cm$^2$ | 39 | 43 | 43 |
| Final reaction press. kg/cm$^2$ | 12 | 19 | 19 |
| Reaction time in hr | 4.5 | 4.25 | 4.5 |
| Output of reaction mass | | | |
| Wt. of organic layer, gm | 1009 | 1106 | 1106 |
| Wt. of aqueous layer, gm | 721 | 708 | 698 |
| Analysis, wt % | | | |
| Hexenes, wt % | 0.0735 | 0.1106 | 0.1106 |
| Toluene, wt % | 74.038 | 70.324 | 70.324 |
| n-Propyl Benzene (NPB), wt % | 18.292 | 19.127 | 19.127 |
| 3-PP (**) and Heavies, wt % | 7.542 | 10.3868 | 10.3868 |
| Reaction performance | | | |
| Toluene to Ethylene mol ratio | 3.54 | 2.65 | 2.65 |
| Quantity of NPB, gm | 184.57 | 211.54 | 211.54 |
| Selectivity based on toluene, % | 39.64 | 49.72 | 49.72 |
| Toluene per pass conversion, % | 32.33 | 29.55 | 29.55 |
| NPB to 3-PP & Heavies ratio | 2.43 | 1.84 | 1.84 |

(**) 3-Phenyl pentane.

Example 5

Preparation of n-Propyl Benzene Using Potassium Carbonate as the Solid Support for Lithium Metal Catalyst with Initiator In this example, preparation of n-propyl benzene was carried out using potassium carbonate as the solid support, lithium as the metal catalyst and di-ter-butyl peroxide (DTBP) as the initiator. The steps of the process (200) are similar as mentioned in Example 2, except the temperature range of 190° C. to 200° C., and the same are not again described herein for the sake of the brevity. The details and the results of the examples 5.1 and the control experiment (without initiator) are shown in the following Table-5.

TABLE 5

Example-5.1, Control: potassium carbonate catalyst support, lithium metal catalyst, DTBP initiator

|  | Example Number | |
|---|---|---|
|  | Example-5.1 | Control Example |
| Charge to 2-L Reactor | | |
| Dry toluene, gm | 920 | 920 |
| Ethylene Gas | | |
| Lot-1, gm | 70 | 70 |
| Lot-2, gm | 70 | 70 |
| Potassium carbonate, gm | 78 | 78 |
| Sodium metal, gm | 0 | 9.2 |
| Lithium metal, gm | 3 | 0 |
| Oleic acid, gm | 2.5 | 2.5 |
| Methanol, gm | 32 | 32 |
| Water, gm | 600 | 600 |
| Charge to 500-ml Reactor | | |
| Dry toluene | 184 | 184 |
| Initiator, DTBP, mg (*) | 225 | 0 |
| Process conditions | | |
| Maximum reaction temp., ° C. | 215.2 | 210.1 |
| Maximum reaction press., kg/cm$^2$ | 39 | 44.8 |
| Final reaction press., kg/cm$^2$ | 21 | 9.5 |
| Reaction time in hr | 8.5 | 5 |
| Output of reaction mass | | |
| Wt. of organic layer, gm | 1178 | 1181 |
| Wt of aqueous layer, gm | 708 | 694 |
| Analysis, wt % | | |
| Hexenes, wt % | 0 | 0 |
| Toluene, wt % | 63.863 | 61.453 |
| n-Propyl Benzene (NPB), wt % | 26.061 | 23.821 |
| 3-PP (**) and Heavies, wt % | 9.802 | 14.726 |
| Reaction performance | | |
| Toluene to Ethylene mol ratio | 2.40 | 2.40 |
| Quantity of NPB, gm | 307 | 281.33 |
| Selectivity based on toluene, % | 66.92 | 57.02 |
| Toluene per pass conversion, % | 31.86 | 34.26 |
| NPB to 3-PP & Heavies ratio | 2.66 | 1.62 |

(*) DTBP-Di-tert-butyl peroxide;
(**) 3-PP-3-Phenyl pentane.

Example 6

Preparation of n-Propyl Benzene Using Potassium Carbonate as the Solid Support for Sodium Metal Catalyst and Recycling of the Alkali Metal Catalyst Along with Partial Recycling of 3-Phenyl Pentane

In this example, preparation of n-propyl benzene was carried out using potassium carbonate as the solid support, sodium as the metal catalyst and di-ter-butyl peroxide (DTBP) as the initiator. The steps of the process (200) are similar as mentioned in Example 2 and the same are not again described herein for the sake of the brevity. The reaction mixture was siphoned out of the first reactor under pressure so that only the liquid phase was transferred. The liquid phase was used for collection of residual catalyst, potassium carbonate and un-reacted toluene, and the remaining organic phase was used for collection of 3-phenyl pentane. The residual catalyst and potassium carbonate so collected were then continuously recycled for at least 10-15 times in the next preparation cycles of n-propyl benzene.

The details and the results of examples 6.1 to 6.5 for recycling the alkali metal catalyst are shown in Table-6. The details and the results of recycling the catalyst and part recycle of 3-phenyl pentane are reflected in the examples 7.1 and 7.2 for, shown in Table-7.

TABLE 6

Examples-6.1-6.5: potassium carbonate catalyst support, sodium metal catalyst: recycle of alkali metal catalyst

|  | Example Number | | | | |
|---|---|---|---|---|---|
|  | Example-6.1 | Example-6.2 | Example-6.3 | Example-6.4 | Example-6.5 |
| Remarks | Fresh Cycle | Catalyst Recycle-1 | Catalyst Recycle-2 | Catalyst Recycle-3 | Catalyst Recycle-4 |
| Charge to 2-L Reactor | | | | | |
| Dry toluene, gm | 806 | 802 | 962 | 1010 | 1206 |
| Initiator, DTBP, mg (*) | 80 | 80 | 90 | 100 | 120 |
| Ethylene Gas | | | | | |
| Lot-1, gm | 180 | 165 | 154 | 158 | 138 |
| Lot-2, gm | 0 | 0 | 0 | 0 | 0 |
| Potassium carbonate, gm | 146 | 0 | 0 | 0 | 0 |
| Sodium metal, gm | 14.76 | 10.312 | 10.428 | 10.218 | 8.342 |
| Oleic acid, gm | 3.8 | 3 | 3 | 3.5 | 2.5 |
| Methanol, gm | 0 | 0 | 0 | 0 | 501 |
| Water, gm | 422 | 425 | 450 | 501 | 508 |
| Process conditions | | | | | |
| Maximum reaction temp., ° C. | 228.5 | 211.2 | 212.3 | 216.1 | 208.2 |
| Maximum reaction press. kg/cm$^2$ | 43 | 41 | 40 | 40 | 34 |

TABLE 6-continued

Examples-6.1-6.5: potassium carbonate catalyst
support, sodium metal catalyst: recycle of alkali metal catalyst

| | Example Number | | | | |
|---|---|---|---|---|---|
| | Example-6.1 | Example-6.2 | Example-6.3 | Example-6.4 | Example-6.5 |
| Final reaction press. kg/cm$^2$ | 8 | 7 | 6 | 7 | 7 |
| Reaction time in hr | 2 | 1.15 | 1.45 | 1 | 1 |
| Output of reaction mass | | | | | |
| Wt. of organic layer, gm | 778 | 942 | 1037 | 1195 | 1396 |
| Wt of aqueous layer, gm | 422 | 434 | 459 | 505 | 1038 |
| Analysis, wt % | | | | | |
| Toluene, wt % | 42.580 | 39.721 | 48.625 | 50.613 | 62.294 |
| n-Propyl Benzene (NPB), wt % | 35.444 | 37.305 | 35.852 | 36.508 | 20.580 |
| 3-PP (**) | 19.909 | 20.846 | 13.820 | 11.150 | 6.001 |
| Heavies, wt % | 2.067 | 2.128 | 1.703 | 1.730 | 11.125 |
| Reaction performance | | | | | |
| Toluene to Ethylene mol ratio | 1.39 | 1.36 | 1.48 | 1.90 | 1.95 |
| Quantity of NPB, gm | 275.75 | 351.41 | 371.79 | 436.27 | 287.30 |
| Selectivity based on toluene, % | 44.53 | 62.97 | 62.27 | 82.55 | 65.48 |
| Toluene per pass conversion, % | 58.90 | 53.35 | 47.58 | 40.12 | 27.89 |
| NPB to 3-PP ratio | 1.78 | 1.79 | 2.59 | 3.27 | 3.43 |
| NPB to Heavies ratio | 17.15 | 17.53 | 21.05 | 21.11 | 1.85 |

(*) DTBP-Di-tert-butyl peroxide;
(**) 3-Phenyl pentane.

TABLE 7

Examples-7.1 and 7.2: potassium carbonate catalyst support,
sodium metal catalyst, recycle of the catalyst and part
recycle of 3-phenyl pentane

| | Example Number | |
|---|---|---|
| | Example-7.1 | Example-7.2 |
| Remarks | Fresh Cycle | Catalyst Recycle-1 |
| Charge to 2-L Reactor | | |
| Dry toluene, gm | 774.97 | 781.74 |
| Initiator, DTBP, mg (*) | 80 | 80 |
| 3-PP (**) | 26.03 | 26.26 |
| Ethylene Gas | | |
| Lot-1, gm | 145 | 135 |
| Lot-2, gm | | |
| Potassium carbonate, gm | 145 | 0 |
| Sodium metal, gm | 14.766 | 10.256 |
| Oleic acid, gm | 3.6 | 3 |
| Methanol, gm | 0 | 0 |
| Water, gm | 395 | 670 |
| Process conditions | | |
| Maximum reaction temp., ° C. | 200.1 | 200.4 |
| Maximum reaction press., kg/cm$^2$ | 40 | 39 |
| Final reaction press., kg/cm$^2$ | 8 | 8 |
| Reaction time in hr | 1.5 | 1.5 |
| Output of reaction mass | | |
| Wt. of organic layer, gm | 784 | 1020 |
| Wt of aqueous layer, gm | 398 | 832 |
| Analysis, wt % | | |
| Toluene, wt % | 49.127 | 49.509 |
| n-Propyl Benzene (NPB), wt % | 33.867 | 33.214 |
| 3-PP (**) | 14.159 | 14.948 |
| Heavies, wt % | 2.847 | 2.330 |
| Reaction performance | | |
| Toluene to Ethylene mol ratio | 1.63 | 1.76 |
| Quantity of NPB, gm | 265.52 | 338.78 |
| Selectivity based on toluene, % | 51.17 | 91.19 |
| Toluene per pass conversion, % | 50.81 | 36.06 |
| NPB to 3-PP ratio | 3.27 | 2.76 |
| NPB to Heavies ratio | 11.90 | 14.25 |

(*) DTBP-Di-tert-butyl peroxide
(**) 3-Phenyl pentane

Example 7

Purification of n-Propyl Benzene

An atmospheric pressure fractional distillation assembly was used for the purification of n-propyl benzene. The fractional distillation assembly consists of 10 L capacity stirred jacketed distillation still having 50 mm diameter and 1500 mm height packed distillation column, reflux condenser, distillate receiver, top and bottom temperature indicators and the like. Ten (10) kg crude n-propyl benzene obtained from any of the examples 1 to 6 was added to the fractional distillation assembly. The crude material, under stirring, was heated with the help of a hot oil circulator. Toluene was recovered until the top temperature reached 110° C. to 125° C. and the bottom temperature reached 150°

C. to 155° C., with the reflux ratio '2'. The recovered toluene was recycled in a next n-propyl benzene synthesis run. Pure n-propyl benzene was collected at the top temperature of 165° C. to 170° C. and the bottom temperature of 180° C. to 190° C. During n-propyl benzene collection, a reflux ratio of 3 to 4 was maintained. In all distillation cuts, distillation residues were analyzed using the GC as mentioned under Examples 1 and 2. The purity of n-propyl benzene cut was found to be 99.82% by GC analysis.

The embodiments described herein have the following advantages: (a) The process (200) facilitates reuse of higher alkylated product such as 3-phenyl pentane, alkali metal catalyst and the solid support that improves the selectivity and reduces the effluent load and thus the waste disposal and hence is economically and commercially attractive; (b) The initiators being aprotic in nature are required in very small amount, and improve the selectivity of starting alkyl benzene towards the desired product; (c) The process (200) is less hazardous because dry reagents are used and water is not used in a reaction zone; (d) The potassium carbonate powder improves distribution of catalyst by offering a large amount of surface area for spreading the metal catalyst thereon, thereby allowing a large mass transfer area for the reaction; (e) The potassium carbonate powder improves the contact area between the alkali metal catalyst and the alkyl benzene, and thereby improves the mixing and ensures the availability of the alkali metal catalyst throughout the first reactor; and (f) Compared with potassium, sodium and lithium are easily available, less hazardous to handle, and used in lesser amounts due to lower/lesser atomic weights.

The foregoing embodiments are accomplished and the problems and shortcomings associated with prior art techniques and approaches are overcome as described in the present embodiments. Detailed descriptions of the embodiments are provided herein; however, it should be understood that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure, or matter. The embodiments described above and the methods disclosed herein may suggest further modification and alterations to those skilled in the art. Such further modifications and alterations may be made without departing from the spirit and scope of the invention.

We claim:

1. A process for the preparation of n-propyl benzene, the process comprising the steps of:
   (a) adding a first amount of dry toluene and a dry solid support comprising an alkali metal carboxylate to a first reactor to form a mixture;
   (b) adding an alkali metal catalyst and oleic acid to the mixture prepared in step (a) to form a reaction mass, and closing and agitating the first reactor for a time period of about 30 minutes to about 1 hour;
   (c) flushing the first reactor with nitrogen gas, and heating the reaction mass to a temperature in a range of about 185° C. to about 190° C. for about 15 minutes to activate the catalyst;
   (d) adding a second amount of dry toluene and a first amount of initiator selected from di-tert-butyl peroxide, azo-iso-bis butyronitrile, or iso-amyl nitrite to a second reactor, flushing the second reactor with nitrogen gas, and stirring for about 15 minutes to about 30 minutes, then transferring the second amount of dry toluene and first amount of initiator from the second reactor to the first reactor;
   (e) heating the first reactor to a temperature in a range of about 180° C. to about 220° C., then adding ethylene to the first reactor to form a reaction medium comprising n-propyl benzene;
   (f) periodically adding a second amount of initiator selected from di-tert-butyl peroxide, azo-iso-bis butyronitrile, or iso-amyl nitrite to the first reactor, and maintaining the reaction medium at a temperature range of about 180° C. to about 220° C. for about 1 hour to about 5 hours while agitating the reaction medium at about 35 kg/cm$^2$ to about 40 kg/cm$^2$ and monitoring ethylene consumption, wherein a sum total amount of said initiators added in step (d) and step (f) is about 50 ppm to about 100 ppm;
   (g) cooling the reaction medium to room temperature, then adding an amount of methanol and then adding an amount of water to the reaction medium;
   (h) separating the reaction medium into an aqueous phase comprising the catalyst, solid support and un-reacted toluene, and an organic phase comprising n-propyl benzene and byproduct; and
   (i) analyzing the organic phase and separating the n-propyl-benzene from the byproduct.

2. The process of claim 1, wherein the n-propyl benzene is separated from the byproduct by fractional distillation, and analyzed by gas chromatography.

3. The process of claim 1, wherein the alkali metal carboxylate is potassium carbonate.

4. The process of claim 1, wherein the alkali metal catalyst is selected from the group consisting of sodium, lithium, and a combination thereof.

5. The process of claim 1, further comprising recovering the un-reacted toluene from the aqueous phase and using at least a portion of the recovered un-reacted toluene in step (a).

6. The process of claim 1, wherein said byproduct comprises a 3-phenyl-pentane.

7. The process of claim 6, wherein at least a portion of the byproduct is recycled to the first reactor.

* * * * *